United States Patent [19]
Bach et al.

[11] Patent Number: 5,350,873
[45] Date of Patent: Sep. 27, 1994

[54] OPTICALLY ACTIVE PHENOXYPROPIONIC ESTERS

[75] Inventors: Volker Bach, Neustadt; Wolfgang Brox, Heidelberg; Karl-Heinz Etzbach, Frankenthal; Axel Paul, Lampertheim; Karl Siemensmeyer, Frankenthal, all of Fed. Rep. of Germany

[73] Assignee: BASF Aktiengesellschaft, Ludwigshafen, Fed. Rep. of Germany

[21] Appl. No.: 928,568

[22] Filed: Aug. 13, 1992

[30] Foreign Application Priority Data

Aug. 16, 1991 [DE] Fed. Rep. of Germany .... 4126996.9

[51] Int. Cl.$^5$ .............................................. C07C 69/76
[52] U.S. Cl. ...................................... 560/60; 546/238; 549/557
[58] Field of Search ....................... 560/60; 546/238; 549/557

[56] References Cited

U.S. PATENT DOCUMENTS

4,367,924  1/1983  Clark et al. ......................... 350/334

FOREIGN PATENT DOCUMENTS

| | | |
|---|---|---|
| 196070 | 1/1986 | European Pat. Off. |
| 219481 | 4/1987 | European Pat. Off. |
| 258898 | 3/1988 | European Pat. Off. |
| 274128 | 7/1988 | European Pat. Off. |
| 331367 | 9/1989 | European Pat. Off. |
| 2623558 | 12/1977 | Fed. Rep. of Germany. |
| 3823154 | 1/1990 | Fed. Rep. of Germany. |
| 3827601 | 2/1990 | Fed. Rep. of Germany. |
| 3930667 | 3/1991 | Fed. Rep. of Germany. |

OTHER PUBLICATIONS

Ferroelectricity in Tilted Smectics . . . Beresnev et al., Mol. Cryst. Liq. 1982, vol. 89, pp. 327–338.
Healhcock, C. et al, JACS 106(26) 8161–74 1984.
D. M. Walba et al., "Design and Synthesis of a New .. . " J. Am. Chem. Soc., vol. 108, No. 17, Aug. 20, 1986.
The first bilayer ferroelectric liquid crystal, Brand, J. Physique Lettres 44 (1983)L–771–L–776, Sep. 15, 1983, p. L–771.
Submicrosecond bistable electro-optic switching in liquid crystals Appl. Phys. Lett. 36(11), Jun. 1980.
Modulators, Linear Arrays and Matrix Arrays . . . Clark, Proceedings of the SID, vol. 26/2, 1985.

*Primary Examiner*—Paul J. Killos
*Attorney, Agent, or Firm*—Keil & Weinkauf

[57] ABSTRACT

Optically active compounds of the formula I

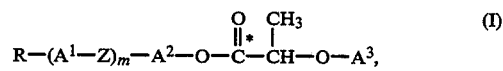

where
R is $C_1$–$C_{12}$-alkyl or -perfluoroalkyl in which one or two non-adjacent $CH_2$ or $CF_2$ groups can also be replaced by —O— and/or —CO— and/or —CO—O— and/or —CH=CH— and/or —CH-halogen— and/or —CHCN— and/or —O—CO—CH-halogen— and/or —O—CO—CHCN—, or is $C_1$–$C_{12}$-alkyl which can have a terminal chemically reactive group and in which a $CH_2$ group can be replaced by —O—, $A^1$ and $A^2$ are each, independently of one another, 1,4-phenylene which is unsubstituted or substituted by one or two F and/or Cl and/or Br atoms and/or $CH_3$ groups and/or CN groups and in which one or two CH groups can also be replaced by N, 1,4-cyclohexylene in which one or two non-adjacent $CH_2$ groups can also be replaced by —O— and/or —S—, 1,4-piperidinediyl, 1,4-bicyclo[2.2.2]octylene, 2,6-naphthalenediyl, decahydro-2,6-naphthalenediyl or 1,2,3,4-tetrahydro-2,6-naphthalenediyl, $A^3$ is unsubstituted or substituted phenyl, Z is —CO—O—, —O—CO—, —$CH_2CH_2$—, —$OCH_2$—, —$CH_2O$—, —C≡C— or a single bond and m is 0, 1, 2 or 3.

17 Claims, No Drawings

OPTICALLY ACTIVE PHENOXYPROPIONIC ESTERS

The present invention relates to optically active compounds of the formula I

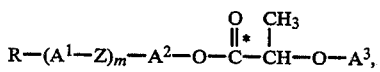

$$R-(A^1-Z)_m-A^2-O-\overset{O}{\underset{\|}{C}}-\overset{CH_3}{\underset{|}{C^*H}}-O-A^3, \quad (I)$$

where

R is $C_1$-$C_{12}$-alkyl or -perfluoroalkyl in which one or two non-adjacent $CH_2$ or $CF_2$ groups can also be replaced by —O— and/or —CO— and/or —CO—O— and/or —CH=CH— and/or —CH-halogen— and/or —CHCN— and/or —O—CO—CH-halogen— and/or —O—CO—CHCN—, or is $C_1$-$C_{12}$-alkyl which can have a terminal chemically reactive group and in which a $CH_2$ group can be replaced by —O—, $A^1$ and $A^2$ are each, independently of one another, 1,4-phenylene which is unsubstituted or substituted by one or two F and/or Cl and/or Br atoms and/or $CH_3$ groups and/or CN groups and in which one or two CH groups can also be replaced by N, 1,4-cyclohexylene in which one or two non-adjacent $CH_2$ groups can also be replaced by —O— and/or —S—, 1,4-piperidinediyl, 1,4-bicyclo-[2.2.2]octylene, 2,6-naphthalenediyl, decahydro-2,6-naphthalenediyl or 1,2,3,4-tetrahydro-2,6-naphthalenediyl, $A^3$ is unsubstituted or substituted phenyl, Z is —CO—O—, —O—CO—, —$CH_2CH_2$—, —$OCH_2$—, —$CH_2O$—, —C≡C— or a single bond and m is 0, 1, 2 or 3, with the proviso that when m is 2 or 3 the radicals $A^1$ and Z in the individual —($A^1$—Z) groups can each, independently of one another, be identical or different.

The present invention also relates to polymers II which are prepared from compounds of the formula I or contain the latter as constituent.

The present invention additionally relates to low molecular weight compounds XI which form glass-like solids and which carry a plurality of groups which are derived from the compounds of the formula I, as substituents.

Liquid crystals have in recent times found uses in a wide variety of industrial areas where electrooptic and display properties are in demand (e.g. in the displays of timepieces, pocket calculators and typewriters). These display devices are based on the dielectric alignment effects in the nematic, cholesteric and/or smectic phases of liquid-crystalline compounds: the dielectric anisotropy causes the long axis of the molecules to assume a particular alignment in an applied electric field. The usual response times of these display devices tend to be too long for many other potential uses of liquid crystals, which are, because of their unique properties, very industrially promising compounds. This disadvantage becomes particularly evident when, as is unavoidably the case when the display elements have larger areas, a large number of picture elements have to be controlled, which would make the image repetition frequency and thus the image quality of equipment with larger areas such as video equipment, oscillographs or television, radar, EDP or automatic printer screens too low.

Besides nematic and cholesteric liquid crystals, the practical applications of ferroelectric smectic liquid-crystalline phases have become increasingly important in recent years.

Chiral tilted smectic liquid-crystalline phases with ferroelectric properties can be prepared by adding a suitable chiral doping agent to basic mixtures with one or more tilted smectic phases (L. A. Beresnev et al., Mol. Cryst. Liq. Cryst. 89 (1982) 327; H. R. Brand et al., J. Physique 44 (1983) L-771). Phases of this type can be used as dielectrics for rapid-switching displays which are based on the SSFLC technology principle described by Clark and Lagerwall (N. A. Clark and S. T. Lagerwall, Appl. Phys. Lett. 36 (1980) 899; U.S. Pat. No. 4,367,924) on the basis of the ferroelectric properties of the chirally tilted phase. In this phase, the elongate molecules are arranged in layers, and the molecules are tilted at an angle to the normal to the layer. Moving from layer to layer there is a change in the direction of tilt by a small angle with respect to an axis at right angles to the layers, so that a helical structure is formed. In displays which are based on the SSFLC technology principle, the smectic layers are arranged at right angles to the plates of the cell. The helical arrangement of the direction of tilt of the molecules is suppressed owing to a very small distance between the plates (about 1 to 2 μm). This forces the long axes-of the molecules to arrange themselves in a plane parallel to the plates of the cell, which results in two electrically and optically distinguishable tilt orientations. Application of a suitable alternating electric field makes it possible to switch backward and forward between these two states in the liquid-crystal-line phase having spontaneous polarization. This switching operation is considerably faster than in conventional twisted cells (TN-LCDs) which are based on nematic liquid crystals.

Clark and Lagerwall showed that the use of such liquid-crystalline systems in very thin cells results in optoelectric switching or display elements which have response times which are up to a factor of about 1000 faster than conventional TN (twisted nematic) cells (cf., for example, Lagerwall et al. "Ferroelectric Liquid Crystals for Displays", SID Symposium, October Meeting 1985, San Diego, Calif., USA). Because of these and other beneficial properties, e.g. the bistable switching possibilities and the contrast which is virtually independent of the angle of view, ferroelectric liquid crystals are in principle very suitable for the abovementioned uses, e.g. via matrix control.

DE-A-3 930 667 describes a process for the reversible or irreversible generation of an image by the imagewise action of energy on a recording layer in the presence or absence of an electric and/or magnetic field, which results in a pattern of surface charges which corresponds to the imagewise action of the energy on the surface of the recording layer. Chiral, liquid-crystalline polymers are employed for this purpose.

However, the response times of the compounds hitherto disclosed are still too long for practical use of ferroelectric liquid crystals in optoelectric displays. There is thus a need for novel compounds with considerably shorter response times.

It is an object of the present invention to find novel stable liquid-crystalline compounds which are suitable as components of liquid-crystalline phases or can be used to assemble liquid-crystalline polymers which form liquid-crystalline phases with a layer structure and have very short response times.

We have found that this object is achieved by compounds I, II and XI according to the invention.

For simplicity, Ph hereinafter means 1,4-phenylene in which one or two CH groups can also be replaced by N.

Hereinbefore and hereinafter, R, m, $A^1$, $A^2$, $A^3$, Ph and Z have the abovementioned meanings unless expressly noted otherwise. $Z^1$ and $Z^2$ in the following formulae are each Z but $Z^1$ and $Z^2$ can be identical or different.

m is preferably 1 or 2.

The compounds of the formula I accordingly comprise, in particular, compounds of the formulae Ia and Ib (m=1 and 2 respectively):

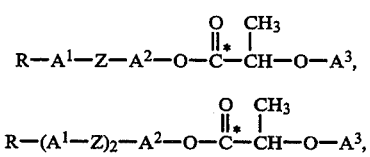

$A^1$ and $A^2$ are each preferably Ph where Ph is preferably 1,4-phenylene.

The compounds of the formula Ib are particularly preferred and comprise, for example, those of the partformulae Ib1 to Ib6:

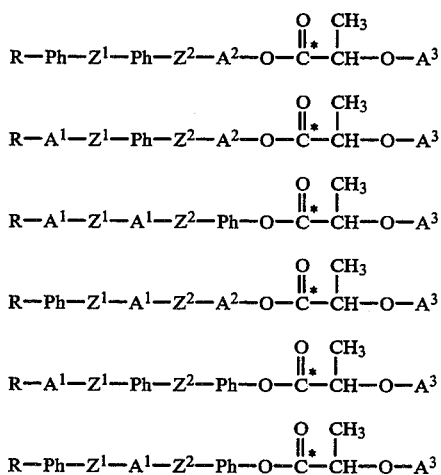

The two $A^1$ groups in the compounds of the formula Ib3 can be identical or different. Particularly preferred compounds of the formula I are those where Z or $Z^1$ and $Z^2$ are each —CO—O—, —O—CO— or a single bond.

$A^3$ is preferably phenyl which is unsubstituted or has one or two substituents $S^1$ and $S^2$, where $S^1$ and $S^2$ are preferably, independently of one another, each $C_1$-$C_{10}$-alkyl, $C_1$-$C_{10}$-alkoxy, fluorine, chlorine or bromine.

In the compounds of the formula I, the alkyl radicals R, in which one $CH_2$ can also be replaced by O are preferably straight-chain. They preferably have 5 to 11 carbon atoms and are accordingly pentyl, hexyl, heptyl, octyl, nonyl, decyl, undecyl, pentoxy, hexoxy, heptoxy, octoxy, nonoxy, decoxy or undecoxy.

The alkyl radicals R described above are substituted at the end of the chain preferably by reactive groups $R^1$ such as

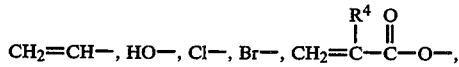

-continued

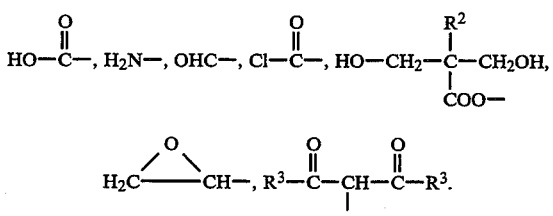

where
$R^2$ is H, $CH_3$ or $C_2H_5$,
$R^3$ is —OH or —Cl, and
$R^4$ is H, Cl or $CH_3$.

Preferred reactive terminal groups $R^1$ in the alkyl radicals R are acryloyloxy, methacryloyloxy, chloroacryloyloxy, hydroxyl or ethenyl.

Particularly preferred polymers II are those prepared by polymerization (for example free-radical polymerization, polycondensation, reaction on polymers) from compounds of the formula I in which the R radicals have chemically reactive groups $R^1$ as terminal substituents.

Examples of preferred polymers II are illustrated in the formulae IIa1 to IId6 where n is an integer which indicates the length of the main chain of the polymer.

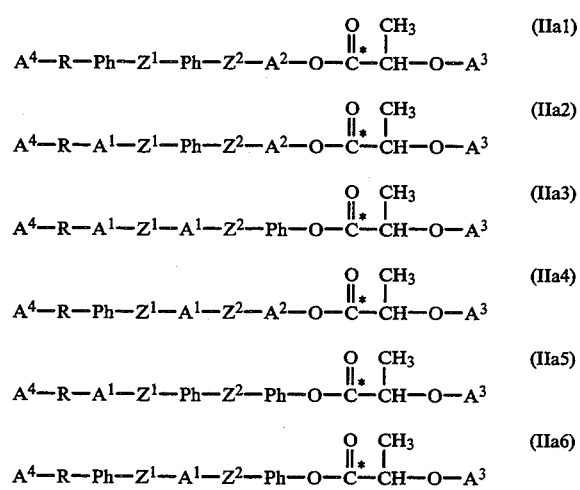

$A^4$ in the formulae IIa1 to IIa6 is a radical of the formula III

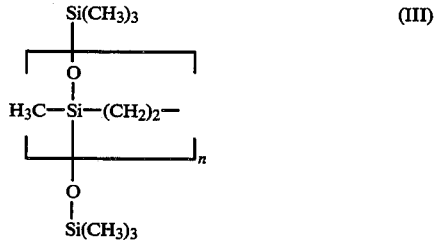

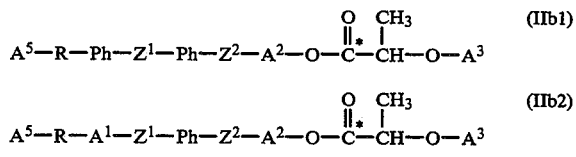

-continued $$A^5-R-A^1-Z^1-A^1-Z^2-Ph-O-\overset{O}{\underset{*}{C}}-\overset{CH_3}{\underset{}{CH}}-O-A^3 \quad (IIb3)$$

$$A^5-R-Ph-Z^1-A^1-Z^2-A^2-O-\overset{O}{\underset{*}{C}}-\overset{CH_3}{\underset{}{CH}}-O-A^3 \quad (IIb4)$$

$$A^5-R-A^1-Z^1-Ph-Z^2-Ph-O-\overset{O}{\underset{*}{C}}-\overset{CH_3}{\underset{}{CH}}-O-A^3 \quad (IIb5)$$

$$A^5-R-Ph-Z^1-A^1-Z^2-Ph-O-\overset{O}{\underset{*}{C}}-\overset{CH_3}{\underset{}{CH}}-O-A^3 \quad (IIb6)$$

$A^5$ in the formulae IIb1 to IIb6 is a radical of the formula IV

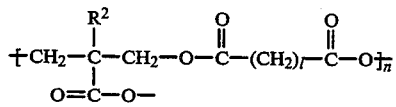

where 1 is an integer from 1 to 20.

$$A^6-R-Ph-Z^1-Ph-Z^2-A^2-O-\overset{O}{\underset{*}{C}}-\overset{CH_3}{\underset{}{CH}}-O-A^3 \quad (IIc1)$$

$$A^6-R-A^1-Z^1-Ph-Z^2-A^2-O-\overset{O}{\underset{*}{C}}-\overset{CH_3}{\underset{}{CH}}-O-A^3 \quad (IIc2)$$

$$A^6-R-A^1-Z^1-A^1-Z^2-A^2-O-\overset{O}{\underset{*}{C}}-\overset{CH_3}{\underset{}{CH}}-O-A^3 \quad (IIc3)$$

$$A^6-R-Ph-Z^1-A^1-Z^2-A^2-O-\overset{O}{\underset{*}{C}}-\overset{CH_3}{\underset{}{CH}}-O-A^3 \quad (IIc4)$$

$$A^6-R-A^1-Z^1-Ph-Z^2-Ph-O-\overset{O}{\underset{*}{C}}-\overset{CH_3}{\underset{}{CH}}-O-A^3 \quad (IIc5)$$

$$A^6-R-Ph-Z^1-A^1-Z^2-Ph-O-\overset{O}{\underset{*}{C}}-\overset{CH_3}{\underset{}{CH}}-O-A^3 \quad (IIc6)$$

$A^6$ in the formulae IIc1 to IIc6 is a radical of the formula V $$+O-CH_2-CH\frac{}{n} \quad (V)$$

$$A^7-R-Ph-Z^1-Ph-Z^2-A^2-O-\overset{O}{\underset{*}{C}}-\overset{CH_3}{\underset{}{CH}}-O-A^3 \quad (IId1)$$

$$A^7-R-A^1-Z^1-Ph-Z^2-A^2-O-\overset{O}{\underset{*}{C}}-\overset{CH_3}{\underset{}{CH}}-O-A^3 \quad (IId2)$$

$$A^7-R-A^1-Z^1-A^1-Z^2-Ph-O-\overset{O}{\underset{*}{C}}-\overset{CH_3}{\underset{}{CH}}-O-A^3 \quad (IId3)$$

$$A^7-R-Ph-Z^1-A^1-Z^2-A^2-O-\overset{O}{\underset{*}{C}}-\overset{CH_3}{\underset{}{CH}}-O-A^3 \quad (IId4)$$

$$A^7-R-A^1-Z^1-Ph-Z^2-Ph-O-\overset{O}{\underset{*}{C}}-\overset{CH_3}{\underset{}{CH}}-O-A^3 \quad (IId5)$$

$$A^7-R-Ph-Z^1-A^1-Z^2-Ph-O-\overset{O}{\underset{*}{C}}-\overset{CH_3}{\underset{}{CH}}-O-A^3 \quad (IId6)$$

Very particularly preferred compounds have the formulae IId1 to IId6 where $A^7$ is a radical of the formula VI.

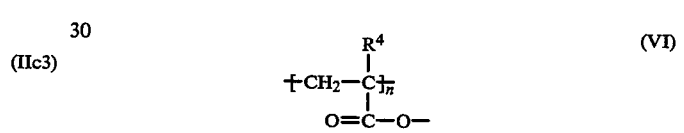

Compound I and II according to the invention are prepared by conventional processes as indicated, for example, in DE-A-38 23 154, EP-A-258 898, EP-A-274 128, DE-A-38 27 601 and DE-A-39 17 196.

This entails, for example in the preparation of the compounds Ib7 and IId7, the chiral phenoxypropionic acid VII being employed directly as acid or chloride thereof, and thus the chiral carbon atom being incorporated.

Example of a synthetic scheme:

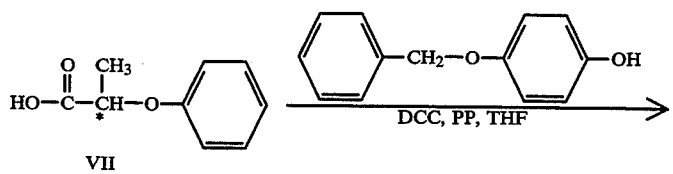

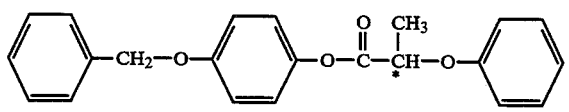

VIIIa

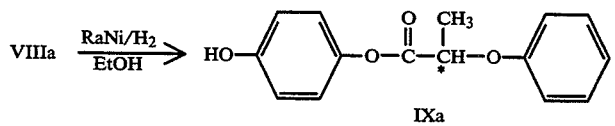

IXa

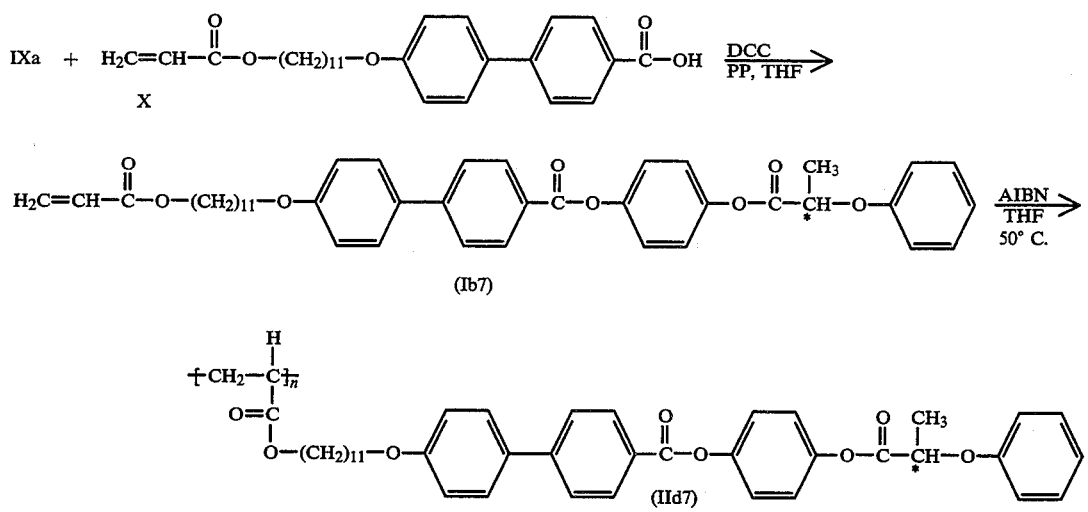

The abbreviations used in this have the following meanings:
AIBN 2,2'-azobis(isobutyronitrile)
DCC dicyclohexylcarbodiimide
EtOH ethanol
PP pyrrolidinopyridine
RaNi Raney nickel
THF tetrahydrofuran The low molecular weight compounds XI according to the invention, which form a glass-like solid, can be obtained by chemical reaction of compounds $Z^3$ which have multiple reactivity with optically active compounds I which have reactive groups $R^1$. They can be obtained, for example, by esterification of the compounds I according to the invention with polyfunctional acids or alcohols or by addition of the compounds I onto polyfunctional isocyanates.

The central groups in the compound XI are derived, for example, from the following compounds $Z^3$:
aliphatic alcohols such as
  glycerol,
  1,2,4-butanetriol,
  2-methyl-2-hydroxymethyl-1,3-propanediol,
  2-ethyl-2-hydroxymethyl-1,3-propanediol,
  1,2,3,4-butanetetrol,
  pentaerythritol,
  xylitol,
  mannitol and
  sorbitol,
aliphatic carboxylic acids such as
  1,2,3-propanetricarboxylic acid,
  1,1,4-butanetricarboxylic acid,
  1,2,3,4-butanetetracarboxylic acid,
  citric acid and
  2-hydroxy-1,2,3-nonadecanetricarboxylic acid,
cycloaliphatic alcohols with 5 or 6 ring members such as
  1,2,3,4-tetrahydroxycyclopentane,
  1,2,3-trihydroxycyclohexane,
  1,2,4-trihydroxycyclohexane,
  1,3,5-trihydroxycyclohexane,
  1,2,3,4-tetrahydroxycyclohexane,
  1,2,3,5-tetrahydroxycyclohexane,
  1,2,4,5-tetrahydroxycyclohexane,
  1,2,3,4,5-pentahydroxycyclohexane and
  1,2,3,4,5,6-hexahydroxycyclohexane,
cycloaliphatic carboxylic acids with 5 or 6 ring members such as
  1,2,3-cyclopentanetricarboxylic acid,
  1,2,4-cyclopentanetricarboxylic acid,
  2-methyl-1,2,3-cyclopentanetricarboxylic acid,
  3-methyl-1,2,4-cyclopentanetricarboxylic acid,
  1,1,2,2-cyclopentanetetracarboxylic acid,
  1,2,2,4-cyclopentanetetracarboxylic acid,
  1,1,3,3-cyclopentanetetracarboxylic acid,
  1,2,3,4-cyclopentanetetracarboxylic acid,
  1,2,3,4,5-cyclopentanepentacarboxylic acid,
  1,1,4-cyclohexanetricarboxylic acid,
  1,2,4-cyclohexanetricarboxylic acid,
  1,3,5-cyclohexanetricarboxylic acid,
  1,1,3,3-cyclohexanetetracarboxylic acid,
  1,1,4,4-cyclohexanetetracarboxylic acid,
  1,2,3,4-cyclohexanetetracarboxylic acid,
  1,2,4,5-cyclohexanetetracarboxylic acid,
  1,1,3,3,5-cyclohexanepentacarboxylic acid and
  1,2,3,4,5,6-cyclohexanehexacarboxylic acid,
alkanolamines such as
  triethanolamine,
  triisopropanolamine and
  aminoethylethanolamine,
triazine derivatives such as
  cyanuric acid,
  thiocyanuric acid,
  melamine and
  trishydroxyethyl isocyanurate,
isocyanates such as
  tetramethylene diisocyanate,
  hexamethylene diisocyanate (HDI),
  dodecamethylene diisocyanate,
  1,4-diisocyanatocyclohexane,
  1-isocyanato-3,5,5-trimethyl-5-isocyanatomethylcyclohexane (isophorone diisocyanate, IPDI),
  4,4'-diisocyanatodicyclohexylmethane (HMDI),
  4,4'-diisocyanato-2,2-dicyclohexylpropane,
  1,4-diisocyanatobenzene,
  2,4-diisocyanatotoluene,
  2,6-diisocyanatotoluene,
  4,4'-diisocyanatodiphenylmethane,
  p-xylylene diisocyanate and the polyisocyanates known in polyurethane chemistry.

Examples of preferred compounds XI are given by formulae XIa1–XId6

$$A^8\text{---}[R\text{---}Ph\text{---}Z^1\text{---}Ph\text{---}Z^2\text{---}A^2\text{---}O\text{---}\underset{O}{\overset{\|}{C}}\text{---}\overset{CH_3}{\underset{*}{C}H}\text{---}O\text{---}A^3]_3 \quad (XIa1)$$

$$A^8\text{---}[R\text{---}A^1\text{---}Z^1\text{---}Ph\text{---}Z^2\text{---}A^2\text{---}O\text{---}\underset{O}{\overset{\|}{C}}\text{---}\overset{CH_3}{\underset{*}{C}H}\text{---}O\text{---}A^3]_3 \quad (XIa2)$$

$$A^8\text{---}[R\text{---}A^1\text{---}Z^1\text{---}A^1\text{---}Z^2\text{---}Ph\text{---}O\text{---}\underset{O}{\overset{\|}{C}}\text{---}\overset{CH_3}{\underset{*}{C}H}\text{---}O\text{---}A^3]_3 \quad (XIa3)$$

$$A^8\text{---}[R\text{---}Ph\text{---}Z^1\text{---}A^1\text{---}Z^2\text{---}A^2\text{---}O\text{---}\underset{O}{\overset{\|}{C}}\text{---}\overset{CH_3}{\underset{*}{C}H}\text{---}O\text{---}A^3]_3 \quad (XIa4)$$

$$A^8\text{---}[R\text{---}A^1\text{---}Z^1\text{---}Ph\text{---}Z^2\text{---}Ph\text{---}O\text{---}\underset{O}{\overset{\|}{C}}\text{---}\overset{CH_3}{\underset{*}{C}H}\text{---}O\text{---}A^3]_3 \quad (XIa5)$$

$$A^8\text{---}[R\text{---}Ph\text{---}Z^1\text{---}A^1\text{---}Z^2\text{---}Ph\text{---}O\text{---}\underset{O}{\overset{\|}{C}}\text{---}\overset{CH_3}{\underset{*}{C}H}\text{---}O\text{---}A^3]_3 \quad (XIa6)$$

In the particularly preferred formulae XIa1–XIa6, $A^8$ a radical of the formula XII:

$$\begin{bmatrix} \text{---OCO---} \\ \text{---OCO---} \\ \text{---OCO---} \end{bmatrix} \quad (XII)$$

$$A^9\text{---}[R\text{---}Ph\text{---}Z^1\text{---}Ph\text{---}Z^2\text{---}A^2\text{---}O\text{---}\underset{O}{\overset{\|}{C}}\text{---}\overset{CH_3}{\underset{*}{C}H}\text{---}O\text{---}A^3]_3 \quad (XIb1)$$

$$A^9\text{---}[R\text{---}A^1\text{---}Z^1\text{---}Ph\text{---}Z^2\text{---}A^2\text{---}O\text{---}\underset{O}{\overset{\|}{C}}\text{---}\overset{CH_3}{\underset{*}{C}H}\text{---}O\text{---}A^3]_3 \quad (XIb2)$$

$$A^9\text{---}[R\text{---}A^1\text{---}Z^1\text{---}A^1\text{---}Z^2\text{---}Ph\text{---}O\text{---}\underset{O}{\overset{\|}{C}}\text{---}\overset{CH_3}{\underset{*}{C}H}\text{---}O\text{---}A^3]_3 \quad (XIb3)$$

$$A^9\text{---}[R\text{---}Ph\text{---}Z^1\text{---}A^1\text{---}Z^2\text{---}A^2\text{---}O\text{---}\underset{O}{\overset{\|}{C}}\text{---}\overset{CH_3}{\underset{*}{C}H}\text{---}O\text{---}A^3]_3 \quad (XIb4)$$

$$A^9\text{---}[R\text{---}A^1\text{---}Z^1\text{---}Ph\text{---}Z^2\text{---}Ph\text{---}O\text{---}\underset{O}{\overset{\|}{C}}\text{---}\overset{CH_3}{\underset{*}{C}H}\text{---}O\text{---}A^3]_3 \quad (XIb5)$$

$$A^9\text{---}[R\text{---}Ph\text{---}Z^1\text{---}A^1\text{---}Z^2\text{---}Ph\text{---}O\text{---}\underset{O}{\overset{\|}{C}}\text{---}\overset{CH_3}{\underset{*}{C}H}\text{---}O\text{---}A^3]_3 \quad (XIb6)$$

$A^9$ in the formulae XIb1–XIb6 is a radical of the formula XIII:

$$\begin{bmatrix} \text{---COO---} \\ \text{---COO---} \\ \text{---COO---} \end{bmatrix} \quad (XIII)$$

$$A^{10}\text{---}[R\text{---}Ph\text{---}Z^1\text{---}Ph\text{---}Z^2\text{---}A^2\text{---}O\text{---}\underset{O}{\overset{\|}{C}}\text{---}\overset{CH_3}{\underset{*}{C}H}\text{---}O\text{---}A^3]_2 \quad (XIc1)$$

$$A^{10}\text{---}[R\text{---}A^1\text{---}Z^1\text{---}Ph\text{---}Z^2\text{---}A^2\text{---}O\text{---}\underset{O}{\overset{\|}{C}}\text{---}\overset{CH_3}{\underset{*}{C}H}\text{---}O\text{---}A^3]_2 \quad (XIc2)$$

$$A^{10}\text{---}[R\text{---}A^1\text{---}Z^1\text{---}A^1\text{---}Z^2\text{---}Ph\text{---}O\text{---}\underset{O}{\overset{\|}{C}}\text{---}\overset{CH_3}{\underset{*}{C}H}\text{---}O\text{---}A^3]_2 \quad (XIc3)$$

-continued $$A^{10}\text{---}[R\text{---}Ph\text{---}Z^1\text{---}A^1\text{---}Z^2\text{---}A^2\text{---}O\text{---}\underset{O}{\overset{\|}{C}}\text{---}\overset{CH_3}{\underset{*}{C}H}\text{---}O\text{---}A^3]_2 \quad (XIc4)$$

$$A^{10}\text{---}[R\text{---}A^1\text{---}Z^1\text{---}Ph\text{---}Z^2\text{---}Ph\text{---}O\text{---}\underset{O}{\overset{\|}{C}}\text{---}\overset{CH_3}{\underset{*}{C}H}\text{---}O\text{---}A^3]_2 \quad (XIc5)$$

$$A^{10}\text{---}[R\text{---}Ph\text{---}Z^1\text{---}A^1\text{---}Z^2\text{---}Ph\text{---}O\text{---}\underset{O}{\overset{\|}{C}}\text{---}\overset{CH_3}{\underset{*}{C}H}\text{---}O\text{---}A^3]_2 \quad (XIc6)$$

$A^{10}$ in the formulae XIc1–XIc6 is a radical of the formula XIV:

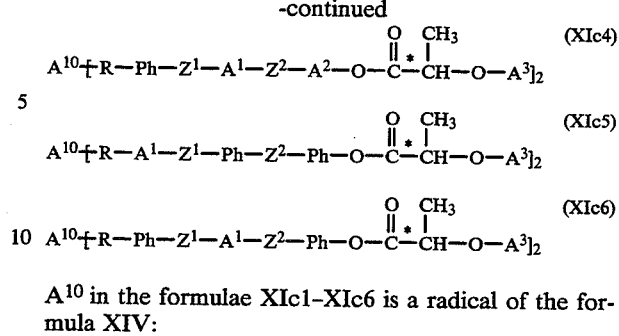

$$A^{11}\text{---}[R\text{---}Ph\text{---}Z^1\text{---}Ph\text{---}Z^2\text{---}A^2\text{---}O\text{---}\underset{O}{\overset{\|}{C}}\text{---}\overset{CH_3}{\underset{*}{C}H}\text{---}O\text{---}A^3]_2 \quad (XId1)$$

$$A^{11}\text{---}[R\text{---}A^1\text{---}Z^1\text{---}Ph\text{---}Z^2\text{---}A^2\text{---}O\text{---}\underset{O}{\overset{\|}{C}}\text{---}\overset{CH_3}{\underset{*}{C}H}\text{---}O\text{---}A^3]_2 \quad (XId2)$$

$$A^{11}\text{---}[R\text{---}A^1\text{---}Z^1\text{---}A^2\text{---}Z^2\text{---}Ph\text{---}O\text{---}\underset{O}{\overset{\|}{C}}\text{---}\overset{CH_3}{\underset{*}{C}H}\text{---}O\text{---}A^3]_2 \quad (XId3)$$

$$A^{11}\text{---}[R\text{---}Ph\text{---}Z^1\text{---}A^1\text{---}Z^2\text{---}A^2\text{---}O\text{---}\underset{O}{\overset{\|}{C}}\text{---}\overset{CH_3}{\underset{*}{C}H}\text{---}O\text{---}A^3]_2 \quad (XId4)$$

$$A^{11}\text{---}[R\text{---}A^1\text{---}Z^1\text{---}Ph\text{---}Z^2\text{---}Ph\text{---}O\text{---}\underset{O}{\overset{\|}{C}}\text{---}\overset{CH_3}{\underset{*}{C}H}\text{---}O\text{---}A^3]_2 \quad (XId5)$$

$$A^{11}\text{---}[R\text{---}Ph\text{---}Z^1\text{---}A^1\text{---}Z^2\text{---}Ph\text{---}O\text{---}\underset{O}{\overset{\|}{C}}\text{---}\overset{CH_3}{\underset{*}{C}H}\text{---}O\text{---}A^3]_2 \quad (XId6)$$

$A^{11}$ in the formulae XId1–XId6 is a radical of the formula XV:

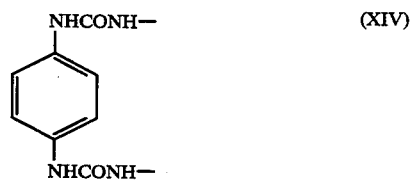

The compounds of the formulae I, II and XI according to the invention are used as components of chiral tilted smectic liquid-crystal phases.

Specific syntheses are described by way of example hereinafter.

Preparation of the Monomeric Compounds I

EXAMPLE 1

To 20 g of 4-benzyloxyphenol (100 mmol) in 500 ml of tetrahydrofuran at 5°–10° C. were successively added 16.4 g of D-phenoxypropionic acid VII (100 mmol), 1.48 g of 4-pyrrolidinopyridine (10 mmol) and 37.1 g of dicyclohexylcarbodiimide (180 mmol). The mixture was then stirred at room temperature until reaction was complete (TLC check). The resulting precipitate was separated off, the solvent was removed under reduced pressure, the residue was taken up in ethyl acetate, and the organic phase was washed several times with water, dried and concentrated under reduced pressure. The crude product was recrystallized from isopropanol.

Yield: 30 g ($\stackrel{\wedge}{=}$87%).

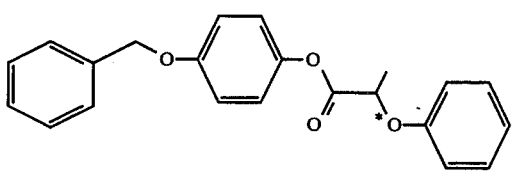
(VIIIa)

The following were prepared in a similar way.

EXAMPLE 2

Yield: 39 g ($\stackrel{\wedge}{=}$85%)

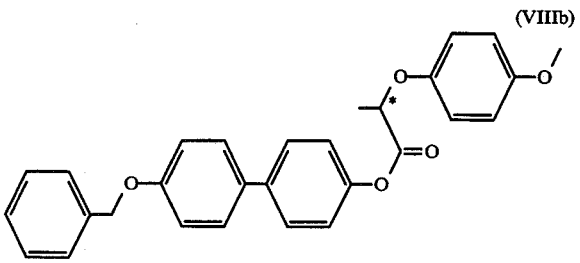
(VIIIb)

EXAMPLE 3

Yield: 35 g ($\stackrel{\wedge}{=}$87%)

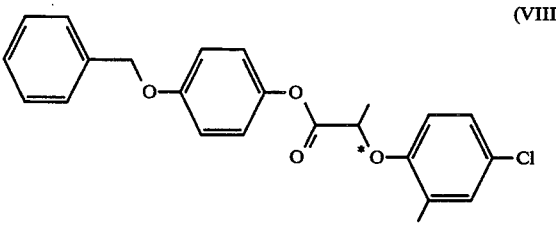
(VIIIc)

EXAMPLE 4

Yield: 37 g ($\stackrel{\wedge}{=}$88%)

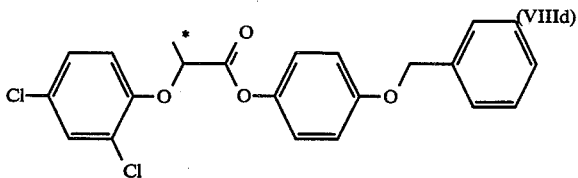
(VIIId)

EXAMPLE 5

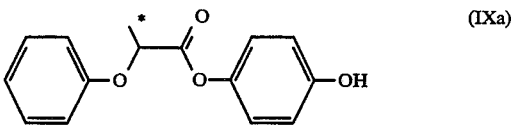
(IXa)

16.5 g of compound VIIIa (47.4 mmol) were mixed with Raney nickel in 250 ml of ethanol and debenzylated with gaseous hydrogen under atmospheric pressure.

Yield: 11 g ($\stackrel{\wedge}{=}$90%) Melting point: 144° C.

The following were prepared in a similar way.

EXAMPLE 6

From compound VIIIb:
Yield: 10 g ($\stackrel{\wedge}{=}$60% )

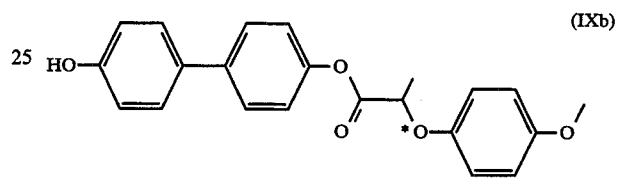
(IXb)

EXAMPLE 7

From compound VIIIc:
Yield: 10 g ($\stackrel{\wedge}{=}$70% )

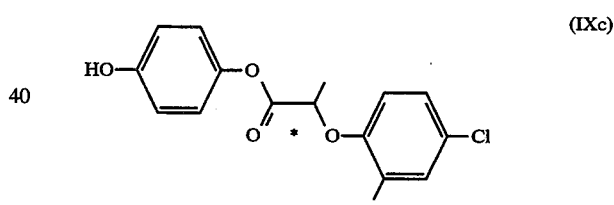
(IXc)

EXAMPLE 8

To 20.2 g of the compound of the formula X (46.1 mmol) in tetrahydrofuran at 0°-5° C. were added, with stirring, 12 g of compound IXa (46.5 mmol), 0.62 g of pyrrolidinopyridine (4.2 mmol) and 13.6 g of dicyclohexylcarbodiimide (66 mmol), and stirring was continued at room temperature until reaction was complete (TLC check). The resulting precipitate was removed, the solvent was removed under reduced pressure, the residue was taken up in methylene chloride, the organic phase was extracted by shaking with water and dried, the solvent was removed under reduced pressure, and the residue was chromatographed on silica gel with 10:1 v/v toluene/ethyl acetate and recrystallized from methanol.

Yield: 6.0 g ($\stackrel{\wedge}{=}$20%) $^1$H-NMR (CDCl$_3$; δ in ppm): 1.0–2.0 (m, 21 al-H), 3.8–4.2 (m, 4H, —OCH$_2$—), 5.0 (m, 1H,—OCOCHMeO—), 6.8–8.3 (m, 17 ar-H and 3H, —CH═C$_2$)

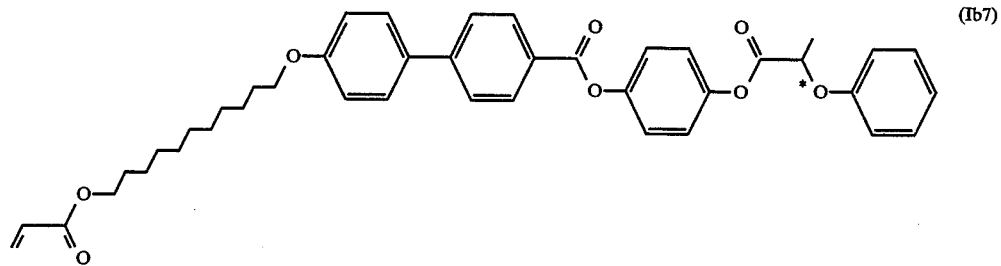

(Ib7)

The following were prepared in a similar way

EXAMPLE 9

From compound IXa:
Yield: 7.2 g ($\triangleq$30%) $^1$H-NMR (CDCl$_3$; δ in ppm): 1.0–2.0 (m, 11 al-H), 3.9–4.3 (m, 4H, —OCH$_2$—), 5.0 (m, 1H, —OCOCHMeO—), 6.7–8.2 (m, 13 ar-H and 3H, —CH=CH$_2$)

From compound IXc:
Yield: 6.1 g ($\triangleq$21%) $^1$H-NMR (CDCl$_3$; δ in ppm): 1.0–2.0 (m, 18 al-H), 2.3 (s, 3H, —CH$_3$), 3.8–4.3 (m, 4H, —OCH$_2$—), 5.0 (m, 1H, —OCOCHMeO—), 5.8 (d, 1H, —CH=CH$_2$), 6.1 (dd, 1H, —CH=CH$_2$), 6.4 (d, 1H, —CH=CH$_2$), 6.7–8.3 (m, 15 ar-H)

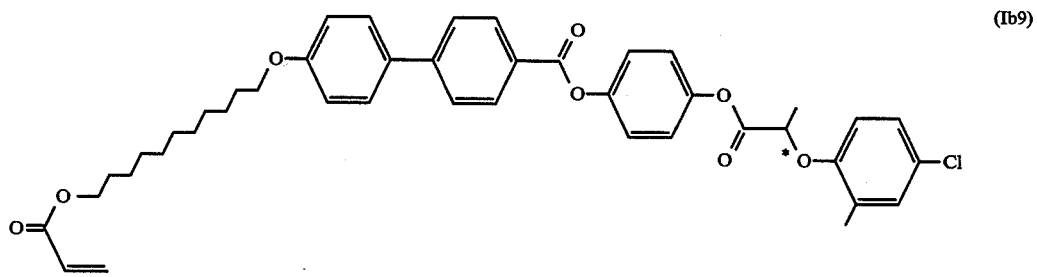

(Ib9)

EXAMPLE 12

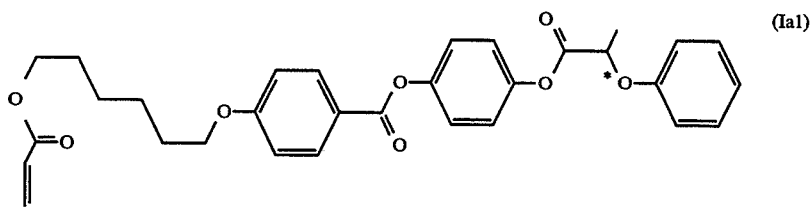

(Ia1)

EXAMPLE 10

From compound IXb:
Yield: 0.2 g ($\triangleq$3%) Clear point: 181° C.

From compound IXb:
Yield: 5.7 g ($\triangleq$17%) $^1$H-NMR (CDCl$_3$; δ in ppm): 1.0–2.0 (m, 21 al-H), 3.8 (s, 3H, —OCH$_3$—), 4.0–4.3 (m, 4H, —CH$_2$O—), 4.9 (q, 1H, —OCOCHMeO—), 5.8 (d, 1H, —CH=CH$_2$), 6.1 (dd, 1H, —CH=CH$_2$), 6.4 (d, 1H, —CH=CH$_2$), 6.8–8.3 (m, 16 ar-H)

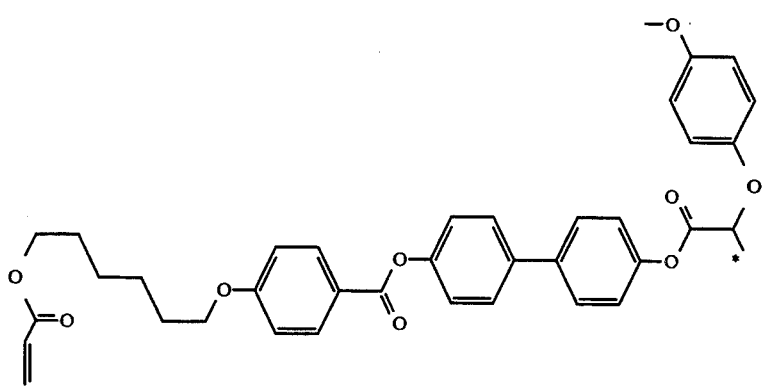

(Ib8)

EXAMPLE 11

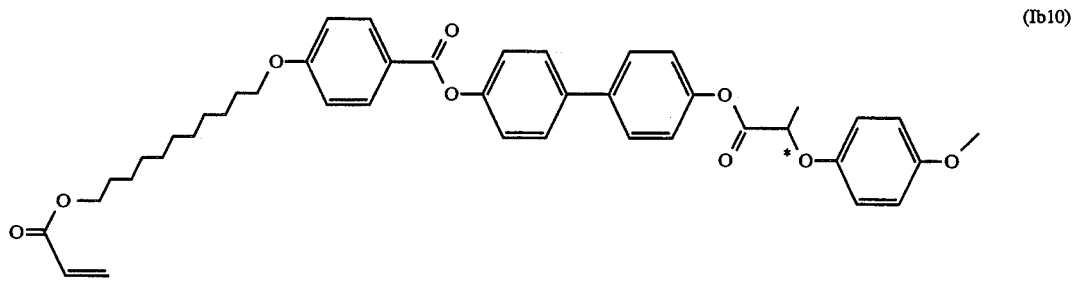

(Ib10)

General procedure for the preparation of polyacrylates

The polymerization was carried out in a Schlenk vessel under a protective gas atmosphere. The monomers were chromatographed and recrystallized several times and then dissolved in concentrations of 0.1–0.01 mol/l in absolute THF (Merck, >99.5%, 4 Å molecular sieves). Argon was then passed into the solution for 15 minutes, 1–40 mol % of 2,2′-azobis(2-isobutyronitrile) (recrystallized from methanol below 40° C.) were added, and argon was passed in for a further 15 minutes.

The solution was then equilibrated at 50° C., and the Schlenk vessel was closed and kept at this temperature for 100–140 h. The reaction mixture was then filtered with suction through a Millipore filter (Type FG, pore size 0.2 μm), precipitated with methanol (Merck, >99.8%), and the residue was filtered off with suction, again dissolved in THF and precipitated with petroleum ether (boiling point 30°–75° C.). This procedure was repeated several times. Residual solvent was removed from the residue under high vacuum.

The following compounds were prepared by the above process.

EXAMPLE 13

From compound Ib7:
Yield: 1.1 g Clear point: 171° C.

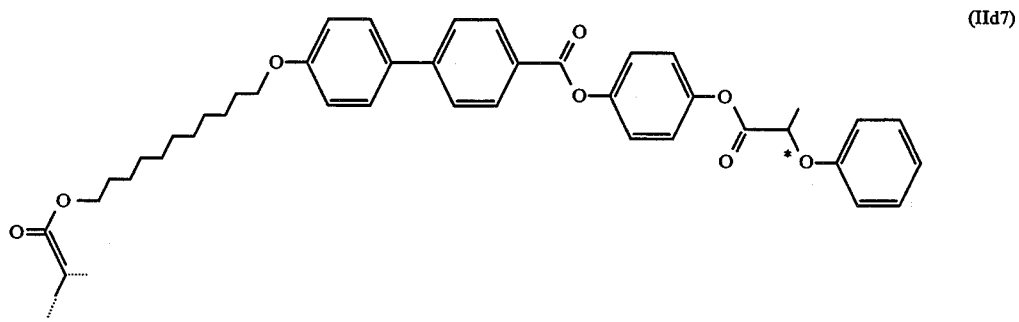

(IId7)

EXAMPLE 14

From compound Ia1:
Yield: 1.2 g Glass transition temperature: 40° C.

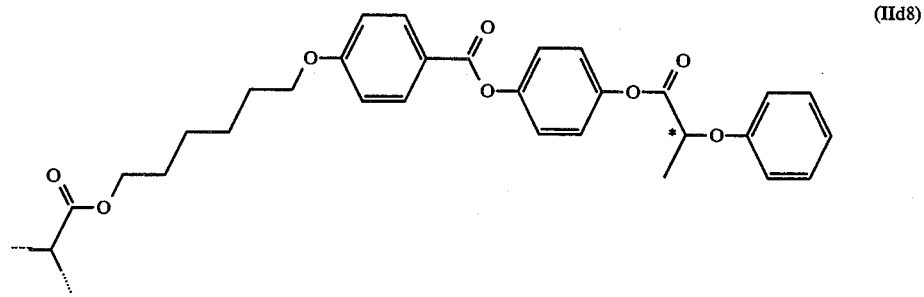

(IId8)

EXAMPLE 15

From compound Ib9:
Yield: 0.9 g Clear point: 192° C.

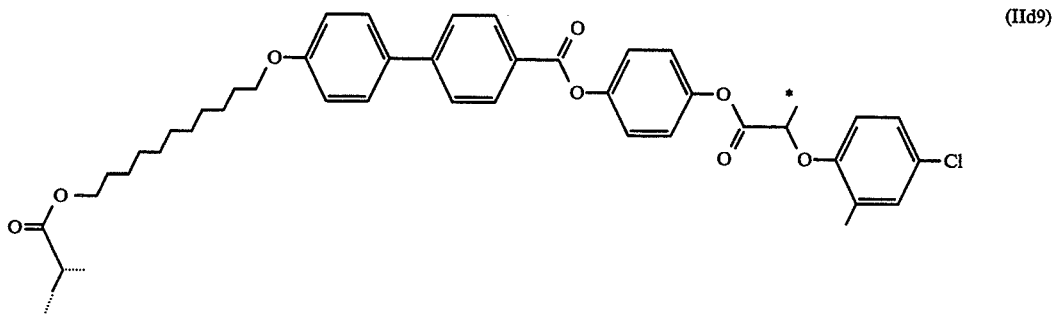

(IId9)

We claim:
1. An optically active compound of the formula I

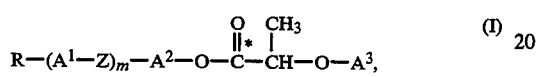

where
R is $C_1$-$C_{12}$-alkyl or -perfluoroalkyl in which each of one or two non-adjacent $CH_2$ or $CF_2$ groups can be replaced by —O—, —CO—, —CO—O—, —CH=CH—, —CH-halogen—, —O—CO—CHCN—, or is $C_1$-$C_{12}$-alkyl which can have a terminal chemically reactive group selected from the group consisting of $CH_2$=CH—, HO—,

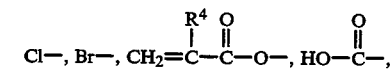

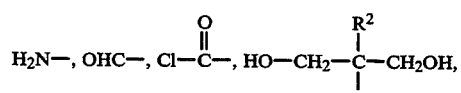

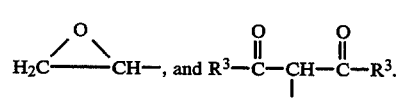

where
$R^2$ is H, $CH_3$ or $C_2H_5$,
$R^3$ is —OH or —Cl, and
$R^4$ is H, Cl or $CH_3$.
and in which a $CH_2$ group can be replaced by —O—,
$A^1$ and $A^2$ are each, independently of the other:
1,4-phenylene which is unsubstituted or substituted by one or two members of the group consisting of F, Cl, Br, $CH_3$ and CN groups and in which one or two CH groups of the phenylene ring can be replaced by N;
1,4-cyclohexylene in which one or two non-adjacent $CH_2$ groups can be replaced by —O— or —S—;
1,4-piperidinediyl;
1,4-bicyclo[2.2.2]octylene;
2,6-naphthalenediyl;
decahydro-2,6-naphthalenediyl; or
1,2,3,4-tetrahydro-2,6-naphthalenediyl,
$A^3$ is unsubstituted or substituted phenyl,
Z is —CO—O—, —O—CO—, —$CH_2CH_2$—, $OCH_2$—, —$CH_2O$, —C≡C—, or a single bond, and m is 1, 2, or 3,
with the proviso that when m is 2 or 3, the radicals $A^1$ and Z in the individual —($A^1$—Z) groups can be identical or different.

2. An optically active compound of the formula I

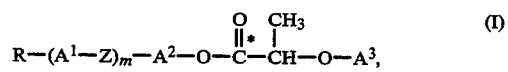

where
R is $C_1$-$C_{12}$-alkyl or -perfluoroalkyl in which each of one or two non-adjacent $CH_2$ or $CF_2$ groups can be replaced by —O—, —CO—, —CO—O—, —CH=CH—, —CH-halogen—, —O—CO—CHCN—, or is $C_1$-$C_{12}$-alkyl which can have a terminal chemically reactive group selected from the group consisting of $CH_2$=CH—, HO—,

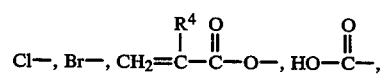

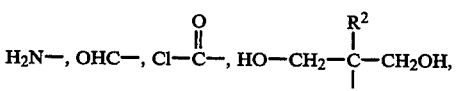

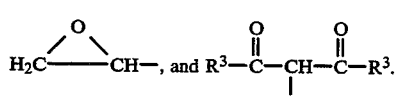

where
$R^2$ is H, $CH_3$ or $C_2H_5$,
$R^3$ is —OH or —Cl, and
$R^4$ is H, Cl or $CH_3$,
and in which a $CH_2$ group can be replaced by —O—,
$A^1$ and $A^2$ are each, independently of the other:
1,4-phenylene which is unsubstituted or substituted by one or two members of the group consisting of F, Cl, Br, $CH_3$ and CN groups and in which one or two CH groups of the phenylene ring can be replaced by N;
1,4-cyclohexylene in which one or two non-adjacent $CH_2$ groups can be replaced by —O— or —S—;
1,4-piperidinediyl;
1,4-bicyclo[2.2.2]octylene;
2,6-naphthalenediyl;
decahydro-2,6-naphthalenediyl; or
1,2,3,4-tetrahydro-2,6-naphthalenediyl,
$A^3$ is phenyl substituted by one or two members which are independently selected from the group consisting of $C_1$-$C_{10}$-alkyl, $C_1$-$C_{10}$-alkoxy, F, Cl, and Br, Z is —CO—O—, —O—CO—, —CH$_2$CH$_2$—, OCH$_2$—, —CH$_2$O, —C≡C—, or a single bond, and m is 0, 1, 2, or 3, with the proviso that when m is 2 or 3, the radicals $A^1$ and Z in the individual —($A^1$—Z) groups can be identical or different.

3. An optically active compound as defined in claim 1, wherein m is 1 or 2.

4. An optically active compound as defined in claim 1, wherein m is 2.

5. An optically active compound as defined in claim 1, wherein Z is —CO—O—, —O—CO— or a single bond.

6. An optically active compound as defined in claim 1, wherein R is $C_5$-$C_{11}$-alkyl or $C_5$-$C_{11}$-alkoxy.

7. An optically active compound as defined in claim 1, wherein $A^1$ and $A^2$ are each 1,4-phenylene.

8. An optically active compound as defined in claim 1, wherein $A^3$ is phenyl.

9. An optically active compound as defined in claim 1, wherein $A^3$ is phenyl which has one or two $C_1$-$C_{10}$-alkyl, $C_1$-$C_{10}$-alkoxy, bromine or chlorine substituents which are independent of one another.

10. An optically active compound of claim 2, wherein m is 1.

11. An optically active compound of claim 2, wherein m is 2.

12. An optically active compound of claim 2, wherein Z is —CO—O—, —O—CO—, or a single bond.

13. An optically active compound of claim 2, wherein R is $C_5$-$C_{11}$-alkyl or $C_5$-$C_{11}$-alkoxy.

14. An optically active compound of claim 2, wherein $A^1$ and $A^2$ are each 1,4-phenylene.

15. An optically active compound of claim 2, wherein $A^3$ is phenyl.

16. An optically active compound of claim 2, wherein $A^3$ is phenyl which has one or two $C_1$-$C_{10}$-alkyl, $C_1$-$C_{10}$-alkoxy, Br, or Cl substituents which are independent of one another.

17. An optically active compound having the formula

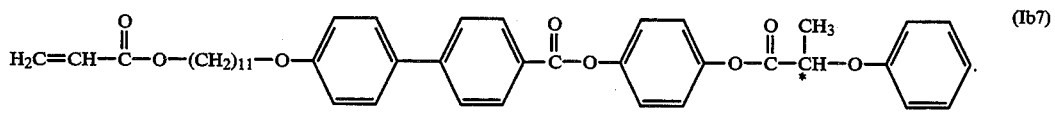

(Ib7)

* * * * *